United States Patent [19]

Wismer

[11] Patent Number: 4,975,156
[45] Date of Patent: Dec. 4, 1990

[54] PROCESS FOR THE SEPARATION OF HYDROGEN FLUORIDE, 1,1-DICHLORO-1-FLUOROETHANE AND 1-CHLORO-1,1-DIFLUOROETHANE FROM LIQUID MIXTURES THEREOF

[75] Inventor: John A. Wismer, Devon, Pa.

[73] Assignee: Atochem North America, Inc., Philadelphia, Pa.

[21] Appl. No.: 347,606

[22] Filed: May 4, 1989

[51] Int. Cl.$^5$ .................. B01D 3/00; C07C 17/38
[52] U.S. Cl. .................................. 203/39; 203/50; 203/67; 203/74; 203/81; 203/98; 203/DIG. 25; 423/483; 423/488; 570/164; 570/178
[58] Field of Search .................. 203/39, 50, 67, 81, 203/82, 84, 71, 98, DIG. 25; 570/164–169, 163, 178; 423/484, 483, 488

[56] References Cited

U.S. PATENT DOCUMENTS

| | | | |
|---|---|---|---|
| 2,478,362 | 8/1949 | Benning | 570/178 |
| 2,549,609 | 4/1951 | Johnson | 570/178 |
| 3,833,676 | 9/1974 | Ukaji et al. | 570/164 |
| 4,199,409 | 4/1980 | Skraba | 203/39 |
| 4,209,470 | 6/1980 | Lorquet | 570/180 |

FOREIGN PATENT DOCUMENTS

| | | | |
|---|---|---|---|
| 2659046 | 7/1977 | Fed. Rep. of Germany | 570/167 |
| 2739478 | 3/1978 | Fed. Rep. of Germany | 570/166 |
| 48-32449 | 11/1974 | Japan | |

*Primary Examiner*—Wilbur Bascomb
*Attorney, Agent, or Firm*—Seidel, Gonda, Lavorgna & Monaco

[57] ABSTRACT

1,1-Dichloro-1-fluoroethane, 1-chloro-1,1-difluoroethane and hydrogen fluoride are separated from their liquid mixtures, such as liquid mixtures resulting from the hydrofluorination, of 1,1,1-trichloroethane or vinylidene chloride. 1,1-Dichloro-1-fluoroethane and 1-chloro-1,1-difluoroethane are first separated by distillation into their respective mixtures with hydrogen fluoride, which are thereafter subjected to parallel phase separations resulting in two hydrogen fluoride-enriched liquid phases, a 1-chloro-1,1-difluoroethane-enriched liquid phase and a 1,1-dichloro-1-fluoroethane-enriched liquid phase. 1-Chloro-1,1-difluoroethane and 1,1-dichloro-1-fluoroethane are purified from the respective halohydrocarbon-enriched liquid phases by distillation. The hydrogen fluoride-enriched stream generated from the phase separation of the hydrogen fluoride/1,1-dichloro-1-fluoroethane mixture is recycled to the hydrofluorination reaction mixture.

17 Claims, 1 Drawing Sheet

PROCESS FOR THE SEPARATION OF HYDROGEN FLUORIDE, 1,1-DICHLORO-1-FLUOROETHANE AND 1-CHLORO-1,1-DIFLUOROETHANE FROM LIQUID MIXTURES THEREOF

FIELD OF THE INVENTION

The invention relates generally to the process of separating hydrogen fluoride, 1,1-dichloro-1-fluoroethane (hereinafter referred to by its American Society of Refrigeration Engineers designation, "141b") and 1-chloro-1,1-difluoroethane (hereinafter "142b") from their liquid mixtures. In particular, the invention relates to the separation of hydrogen fluoride, 141b and 142b from liquid mixtures resulting from the hydrofluorination of 1,1,1-trichloroethane (hereinafter "140a") or alternatively, from the hydrofluorination of vinylidene chloride.

BACKGROUND OF THE INVENTION

In the manufacture of 141b and 142b by the hydrofluorination of either vinylidene chloride or 140a, the reactor effluent generally contains hydrochlorofluorocarbons and unreacted hydrogen fluoride. The latter arises from feeding hydrogen fluoride in excess of its stoichiometric requirement to the reaction mixture. This is typically the case, as it is usually necessary to employ a large excess of hydrogen fluoride in the hydrofluorination reaction. It is highly desirable to recover the excess hydrogen fluoride for recycle to the reaction mixture.

The principle halohydrocarbon components of the reaction product mixture are 141b and 142b. If 140a is the product precursor, then the reactor effluent will also contain a substantial amount of HCl.

Hydrogen fluoride and 142b form an azeotrope. They cannot therefore be separated by simple distillation. Thus, U.S. Pat. No. 4,209,470 describes a process for separating hydrogen fluoride and 142b by decantation, which may be used for separating liquid mixtures of hydrogen fluoride and 142b generated in the hydrofluorination of 140a or vinylidene chloride. The quality of phase separation is enhanced by the addition to the liquid mixture, of an amount of a halocarbon selected from the group of 141b, vinylidene chloride and 140a. A liquid organic phase enriched in 142b and a liquid inorganic phase enriched in HF are formed. The HF-containing inorganic phase is then subjected to azeotropic distillation. The distillation bottom stream, comprising hydrogen fluoride, is recycled to the hydrofluorination reactor feed.

Japanese Patent Application No. 48/32449 teaches a similar separation wherein the halocarbon added to the HF/142b mixture subject to separation comprises 140a.

The process of U.S. Pat. No. 4,209,470 relies on the generation of an HF recycle stream derived from the phase separation of hydrogen fluoride and 142b. Because these molecules have such high mutual solubility, contamination of the HF recycle stream with 142b is likely. The return of even a small amount of 142b to the hydrofluorination reaction mixture, particularly where the object of the hydrofluorination reaction is the production of 141b, would have an adverse effect on the product distribution, promoting the formation of more fluorinated products, such as 1,1,1-trifluoroethane (hereinafter "143a").

What is needed is a process for separating hydrogen fluoride, 141b and 142b from their liquid mixtures generated from the hydrofluorination of 140a or vinylidene chloride. The process should permit the recycling of highly pure, substantially 142b-free hydrogen fluoride to the hydrofluorination reaction mixture.

SUMMARY OF THE INVENTION

A process for separating 141b, 142b and hydrogen fluoride is provided. A liquid mixture comprising 141b, 142b and hydrogen fluoride is formed and subjected to an initial distillation to form a top product comprising 142b and hydrogen fluoride, and a bottom product comprising 141b and hydrogen fluoride. The initial distillation top product is condensed to form a liquid condensate. The condensate is separated into a first upper liquid phase enriched in hydrogen fluoride relative to 142b, and a lower liquid phase enriched in 142b relative to hydrogen fluoride. The initial distillation bottom product is separated into a second upper liquid phase enriched in hydrogen fluoride relative to 141b, and a lower liquid phase enriched in 141b relative to hydrogen fluoride. 142b is recovered from the 142b-enriched lower liquid phase. 141b is recovered from the 141b-enriched lower liquid phase.

DETAILED DESCRIPTION OF THE INVENTION

Figure 1:
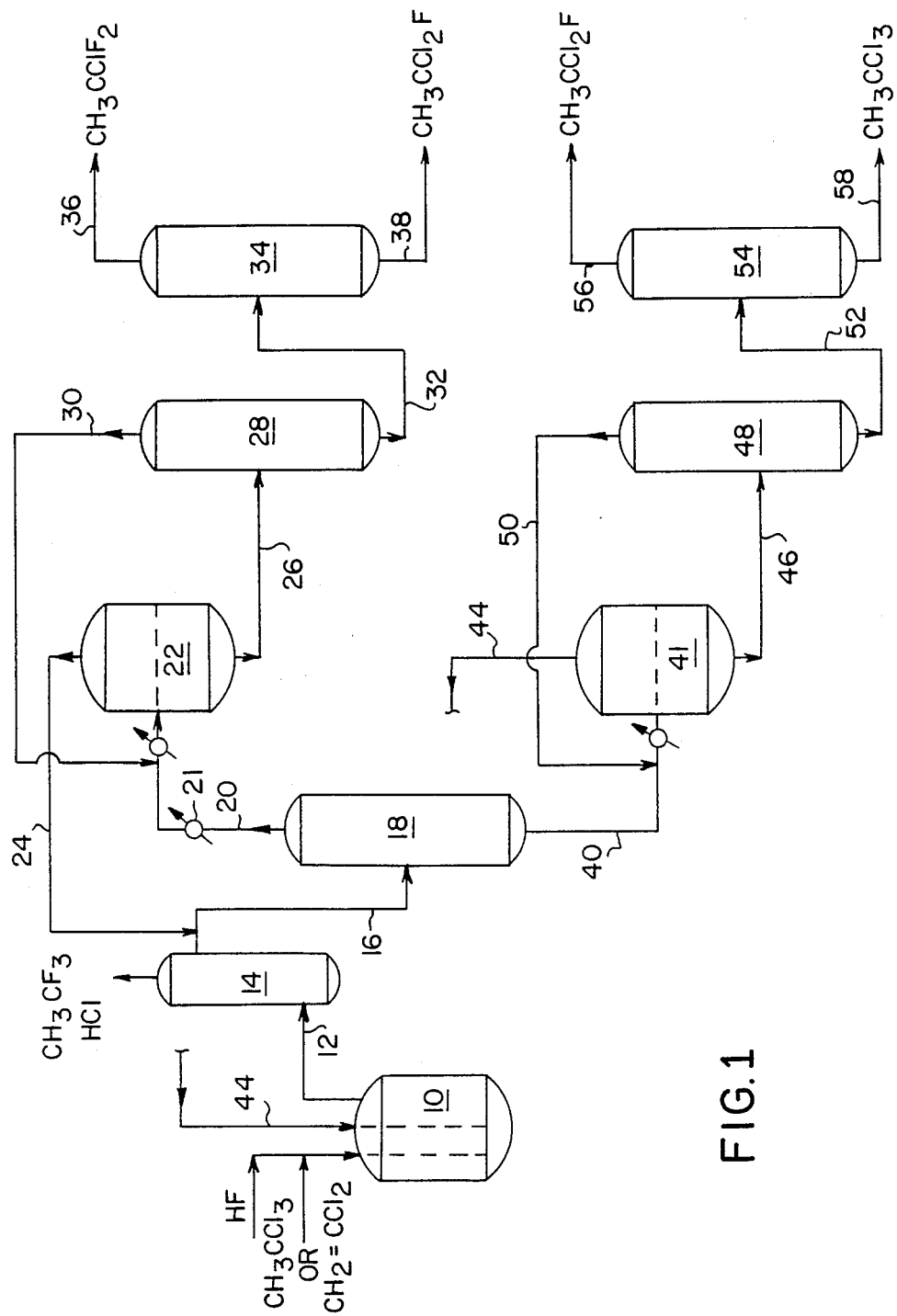
FIG. 1 is a schematic illustrating an embodiment of the process of the invention.

The present separation process finds utility in the manufacture of halohydrocarbons wherein complex mixtures of 141b, 142b and hydrogen fluoride may be formed. The process is particularly useful in separating 141b/142b/HF liquid mixtures which are formed in the manufacture of 141b and/or 142b. The liquid mixture subject to separation is formed by reacting hydrogen fluoride in a hydrofluorination reaction mixture with a co-reactant selected from the group of 140a and vinylidene chloride, and combinations thereof.

While the process of U.S. Pat. No. 4,209,470 involves the addition of 141b to a HF/142b liquid mixture and phase separation thereof, the process of the invention involves first separating 141b and 142b into their respective mixtures with hydrogen fluoride by distillation, and thereafter subjecting the separated HF/halohydrocarbon mixtures to parallel phase separations. The result is separate 141b-enriched and 142b-enriched liquid streams, from which 141b and 142b are purified by subsequent distillation processes.

The initial separation of 141b and 142b by distillation, in advance of phase separation of hydrogen fluoride, allows the selection of the HF-enriched upper liquid phase from the 141b phase separator for recycling to the reaction mixture. Since all hydrogen fluoride recycled to the reactor may be derived from the phase separation of 141b and hydrogen fluoride, rather than from the phase separation of 142b and hydrogen fluoride as in the prior art, essentially no 142b is returned to the hydrofluorination reactor. The hydrogen fluoride recycled to the reactor is of higher purity, and virtually free of 142b. The 142b-promoted formation of 143a in the reaction mixture is thus minimized.

According to the practice of the invention, 140a and/or vinylidene chloride are hydrofluorinated by reaction with anhydrous hydrogen fluoride in an appropriate reactor vessel. The reaction conditions and reactor construction are well known to those skilled in the art.

The separation process of the invention is advantageously utilized with either continuous or discontinuous (batch) reaction processes. Preferably, the instant process is employed in connection with the continuous hydrofluorination of 140a or vinylidene chloride. The hydrofluorination reaction product subject to separation may be continuously withdrawn from the reaction vessel in the form of a liquid mixture, or a gas which is subsequently condensed into a liquid.

The liquid contains a portion of the starting material, that is, 140a or vinylidene chloride. It also contains 141b and 142b, and minor amounts of other halogenated hydrocarbons. HCl is also generated from the hydrofluorination of 140a. It is advantageous to remove at least a portion of the HCl, such as by distillation, before proceeding further. Any 143a generated by the hydrofluorination reaction may also be removed. If not, an additional distillation column may be added downstream to remove 143a and other high boiling species.

The relative amount of 141b and 142b in the mixture subject to separation may vary considerably. Typically, the mixture contains from about 30% to about 85% 141b by weight, based upon the combined weight of 141b and 142b in the mixture.

The liquid mixture subject to separation, following optional removal of at least a portion of the HCl, is subjected to an initial distillation in a main distillation column to separate 141b and 142b. The distillation column is operated at temperatures low enough to minimize reactivity of hydrogen fluoride and 141b. At the column bottom, the temperature is advantageously no greater than about 53° C., preferably no greater than about 40° C., at a column pressure of about 55 PSIG. The distillation results in a top product substantially depleted in 141b relative to 142b, and a bottom product comprising a mixture of 141b and HF substantially depleted in 142b relative to 141b.

Preferably, the main distillation column is operated in a fashion such that substantially all of the 142b in the mixture subject to separation is removed overhead. This may be achieved by operating the column at a reflux ratio of about 12 pounds reflux per pound of liquid distillate, with about 35 equilibrium stages. Thus, the distillation bottom product is substantially free of 142b. Otherwise, 142b must be separated from 141b in a further distillation column. By "substantially free of 142b" is meant that the bottom product contains no more than about 0.5 wt. % 142b, based upon the amount of 141b in the bottom product. Any 141b taken overhead with the 142b may be removed in a subsequent downstream distillation.

Most preferably, the hydrogen fluoride will distribute as a result of the main distillation according to its respective binary azeotropes with 141b and 142b. Thus, the top product preferably has a composition similar to the azeotropic composition of hydrogen fluoride and 142b (about 12 wt. % HF/88 wt. % 142b, or about 40 mol % HF/60 mol % 142b), and the bottom product preferably has a composition similar to the azeotropic composition of hydrogen fluoride and 141b (about 35 wt. % HF/65 wt. % 141b, or about 76 mol % HF/24 mol % 141b).

The term "azeotrope" or "azeotropic composition" as used herein includes not only liquids comprising one phase, i.e., "homoazeotropes", but also includes two-phase liquids, i.e., "heteroazeotropes". The azeotropic mixture of hydrogen fluoride and 142b substantially comprises a homoazeotrope, while the azeotropic mixture of hydrogen fluoride and 141b is a heteroazeotrope.

The top product of the main distillation is condensed. The condensed top product and the bottom product are then separately fed to parallel phase separators (hereinafter "142b phase separator" and "141b phase separator", respectively) for the separation of hydrogen fluoride. Both phase separators are generally operated at temperatures low enough to minimize the reactivity and solubility of hydrogen fluoride with the halohydrocarbon subject to separation. Typically, a temperature of about −20° C. and a pressure of about 1.0 PSIG (i.e., atmospheric pressure) may be used. At this temperature, hydrogen fluoride readily separates from its mixtures with 141b and 142b. Phase separation of the main distillation column top product in the 142b phase separator thus results in an upper liquid phase enriched in hydrogen fluoride relative to 142b and a lower liquid phase enriched in 142b relative to hydrogen fluoride. Similarly, phase separation of the main distillation column bottom product in the 141b phase separator results in an upper liquid phase enriched in hydrogen fluoride relative to 141b, and a lower liquid phase, enriched in 141b relative to hydrogen fluoride.

By way of illustration, and not limitation, the ratio of hydrogen fluoride to 142b in the upper liquid phase from the 142b separator may be about 68 wt. % HF/32 wt. % 142b, while the lower liquid phase from the same phase separator may contain about 3 wt. % HF/97 wt. % 142b. At −20° C. the upper liquid phase from the 141b phase separator may comprise about 92 wt. % HF/8 wt. % 141b, while the lower liquid phase may comprise 1.3 wt. % HF/98.7 wt. % 141b.

Separation of the liquid phases is most advantageously carried out by decantation, utilizing any of the available decantation apparatuses which are well known to those skilled in the art.

141b and 142b are recovered from streams formed by the respective lower liquid phases from the 141b and 142b phase separators. Recovery of the pure halohydrocarbons is easily achieved by removal of their respective low boiling azeotropes with hydrogen fluoride.

The upper liquid phases from the parallel phase separators are enriched in hydrogen fluoride. A stream formed from the 142b phase separator's upper liquid phase is advantageously recycled to and combined with the liquid subject to separation, before the liquid is fed to the main distillation column. A stream formed from the 141b phase separator's upper liquid phase is advantageously recycled to and combined with the hydrofluorination reaction mixture. All hydrogen fluoride recycled to the reaction mixture is thus derived from the HF-rich liquid mixture of hydrogen fluoride and 141b obtained as the 141b phase separator's upper liquid phase. Any hydrogen fluoride obtained from the 142b phase separator's upper liquid phase, which is in the form of an HF-rich liquid mixture of HF and 142b, is recycled to the separation train, not the reactor. Since 141b is somewhat less soluble in hydrogen fluoride than 142b, the hydrogen fluoride recycled from the 141b phase separator to the reactor is of higher purity than a hydrogen fluoride stream which would otherwise be obtained from the 142b phase separation. The small amounts of 141b which may be contained in the 141b phase separator's HF recycle stream is significantly less harmful to the reaction product distribution than the same amount of 142b. The latter has the undesired effect of promoting the formation of the more fluorinated product 143a.

Recovery of 141b and 142b from the respective lower liquid phases from the 141b and 142b phase separators may be achieved according to conventional procedures utilizing one or more distillation columns downstream from the phase separators. Accordingly, a stream comprising the 142b-enriched lower liquid phase from the 142b phase separator is routed to a purification column which distills off an azeotrope of 142b and HF. 142b is recovered as the distillation bottom product. The 142b/HF azeotrope is recycled to and combined with the top product of the main distillation column, which comprises the feed to the 142b phase separator. Preferably, the 142b bottom product is further purified in a product distillation column which removes 142b as an overhead product, with any contaminating 141b recovered as a bottom product.

Likewise, a stream comprising the 141b-enriched lower liquid phase from the 141b phase separator is directed to a distillation column which removes an HF/141b azeotrope overhead. The azeotrope is recycled to and combined with the bottom product of the main distillation column, which comprises the feed to the 141b phase separator. 141b, together with any high boiling impurities such as 1,1,1,3,3-pentafluorobutane, is obtained as the bottom product. The 141b may be purified from its mixtures with the high boiling impurities by a further distillation.

The process of the invention is illustrated in greater detail in the FIGURE. Hydrogen fluoride and either 140a or vinylidene chloride from supply tanks (not shown) are pumped to reactor 10, wherein a portion of the 140a or vinylidene chloride is converted to 141b or 142b. The conditions in the reactor may be selected such that either 141b or 142b is formed preferentially as the predominant product. Such manipulations are known to those skilled in the art. Generally, production of 141b is favored over 142b at lower temperatures, shorter reaction times and, where a catalyst is used, at lower catalyst concentrations. The molar ratio of hydrogen fluoride to precursor (i.e., 140a or vinylidene chloride) may also effect the product selectivity, with an increasing excess of hydrogen fluoride generally favoring formation of the more fluorinated product 142b.

The effluent withdrawn from the reactor provides a reaction product stream in line 12 containing unreacted precursor, unreacted hydrogen fluoride, 141b, 142b, and possibly minor amounts of 143a and other halohydrocarbons. In a typical reaction for the hydrofluorination of 140a, the reactor effluent is in the form of a gas which may have the following approximate composition, by weight percent: HF, 29.6; HCl, 19.6; 141b, 41.9; 142b, 8.8; 143a, 0.1.

If the reaction precursor is 140a, the reactor effluent contains HCl which is removed overhead in HCl stripper column 14, which also removes 143a. Stripper column 14 is operated, for example, at about 111 PSIG, with a top temperature of about $-1°$ C. and a bottom temperature of about 71° C. The stream in line 16 from the stripper column constitutes the reactor effluent from which a substantial portion of the HCl has been preferably removed. The stripped reactor effluent is fed to a main distillation column 18 which is preferably operated such that all of the 142b in the mixture is removed overhead. The maximum operating temperature of column 18 is about 27° C. (top) and about 53° C. (bottom), with a pressure of about 55 PSIG. Above this range of temperatures, significant reaction may occur between 141b and hydrogen fluoride, generating additional 142b. Most preferably, the overhead stream from main distillation column 18 is similar in composition to the azeotropic composition of HF and 142b. The bottom stream from main distillation column 18 is preferably free of all 142b, and most preferably has a composition similar to the azeotropic composition of HF and 141b.

Turning to the 142b-recovery portion of the system, the overhead stream from main distillation column 18 is condensed by condensor 21 and fed through line 20 to 142b phase separator 22 and cooled. The stream separates into an HF-enriched upper liquid phase, which contains, e.g., by weight, about 74% HF and about 26% 142b, and a 142b-enriched lower liquid phase, which contains, e.g., by weight, about 9% HF and about 91% 142b. The two phases are separated to form an HF-enriched stream and a 142b-enriched stream. The HF-enriched stream is recycled via line 24 to the hydrofluorination reaction product stream, which comprises the feed of main distillation column 18. The 142b-enriched stream is pumped through line 26 to distillation column 28, which is operated at, for example, a top temperature of about 34° C. and a bottom temperature of about 45° C., at a pressure of about 75 PSIG. A mixture which has a composition similar to the azeotropic composition of HF and 142b, i.e., about 12% HF/88% 142b, by weight, is distilled off as a top product from column 28. The top product is recycled to and combined with the overhead stream from main distillation column 18 via line 30. 142b, which is recovered from column 28 as a bottom product, is routed through line 32 to a finishing distillation column 34 to remove any remaining 141b contamination. Column 34 is operated, for example, at a top temperature of about 38° C. and a bottom temperature of about 64° C., at a 55 PSIG pressure. 142b is obtained from column 34 as an overhead product in line 36. Any 141b remaining in the system is taken through line 38 as the bottom product.

The 142b-enriched stream from phase separator 22 may be optionally subjected to distillation in a lights column (not shown). The bottom stream from the optional lights column comprises the feed to distillation column 28. The lights column is operated to remove 140a and any HCl which may have been generated in main distillation column 18 and carried overhead therefrom with 142b.

Turning to the 141b-recovery portion of the system, the bottom stream from main distillation column 18 is fed through line 40 to 141b-phase separator 42 and cooled. Phase separator 41 is similar in construction and operation to phase separator 22. The stream separates into an HF-enriched upper liquid phase, which contains, e.g., by weight, about 95% HF and about 5% 141b, and a 141b-enriched lower liquid phase, which contains, e.g., by weight, about 99% 141b and about 1% HF. The two phases are separated to form an HF-enriched stream and a 141b-enriched stream. The latter may also contain minor amounts (less than 1%) of low boiling by products, such as 1,1,1,3,3-pentafluorobutane. The HF-enriched stream is recycled to the hydrofluorination reactor 10 for combination with the reaction mixture via line 44. The 141b-enriched stream is pumped through line 46 to distillation column 48, which is operated at, for example, a top temperature of about 52° C. and a bottom temperature of about 84° C., at a pressure of about 55 PSIG. The top product from distillation column 48 has a composition similar to the azeotropic composition of HF and 141b, that is, about 34% HF/66% 141b, by weight. The top product is recycled to and combined with the bottom stream from main distillation column 18 via line 50. The bottom product of distillation column 48 contains 141b and high-boiling by-products. The bottom product is routed through line 52 to a finishing distillation column 54, which is operated, for example, at a top temperature of about 54° C. and a bottom temperature of about 77° C., at a pressure of about 15 PSIG. The overhead product of column 54 which comprises 141b, is combined via line 56 with the bottom product of distillation column 34 to form a common 141b stream. The bottom product from distillation column 54 comprises high boiling species, most notably 140a, in line 58.

The conditions and proportions in the foregoing description are for illustration only and should not be construed as limiting the scope of the invention.

The present invention may be embodied in other specific forms without departing from the spirit or essential attributes thereof and, accordingly, reference should be made to the appended claims, rather than to the foregoing specifications, as indicating the scope of the invention.

I claim:

1. A process for separating 1,1-dichloro-1-fluoroethane, 1-chloro-1,1-difluoroethane and hydrogen fluoride from a liquid mixture thereof comprising:
   (a) forming a liquid mixture comprising 1,1-dichloro-1-fluoroethane, 1-chloro-1,1-difluoroethane and HF;
   (b) subjecting the liquid mixture to an initial distillation to form a top product comprising 1-chloro-1,1-difluoroethane and hydrogen fluoride, and a bottom product comprising 1,1-dichloro-1-fluoroethane and hydrogen fluoride;
   (c) condensing the initial distillation top product to form a liquid condensate, and separating the condensate into a first upper liquid phase enriched in hydrogen fluoride relative to 1-chloro-1,1-difluoroethane and a lower liquid phase enriched in 1-chloro-1,1-difluoroethane relative to hydrogen fluoride;
   (d) separating the initial distillation bottom product into a second upper liquid phase enriched in hydrogen fluoride relative to 1,1-dichloro-1-fluoroethane and a lower liquid phase enriched in 1,1-dichloro-1-fluoroethane relative to hydrogen fluoride;
   (e) recovering 1-chloro-1,1-difluoroethane from the 1-chloro-1,1-difluoroethane-enriched lower liquid phase; and
   (f) recovering 1,1-dichloro-1-fluoroethane from the 1,1-dichloro-1-fluoroethane-enriched lower liquid phase.

2. A process according to claim 1 wherein the liquid mixture subject to separation is formed by reacting hydrogen fluoride in a hydrofluorination reaction mixture with a co-reactant selected from the group consisting essentially of 1,1,1-trichloroethane and vinylidene chloride, and combinations thereof.

3. A process according to claim 2 wherein the co-reactant is 1,1,1-trichloroethane, and the process includes the step of removing hydrogen chloride from the liquid mixture subject to separation prior to the initial distillation.

4. A process according to claim 2 wherein the step of recovering 1-chloro-1,1-difluoroethane from the 1-chloro-1,1-difluoroethane-enriched lower liquid phase comprises distilling an azeotrope of hydrogen fluoride and 1-chloro-1,1-difluoroethane from said liquid, and recovering 1-chloro-1,1-difluoroethane from the distillation bottom product.

5. A process according to claim 4 wherein the azeotrope mixture of hydrogen fluoride and 1-chloro-1,1-difluoroethane distilled from the 1-chloro-1,1-difluoroethane-enriched lower liquid phase is recycled to and combined with the initial distillation top product.

6. A process according to claim 2 wherein the step of recovering 1,1-dichloro-1-fluoroethane from the 1,1-dichloro-1-fluoroethane-enriched lower liquid phase comprises distilling an azeotrope of HF and 1,1-dichloro-1-fluoroethane from said liquid, and recovering 1,1-dichloro-1-fluoroethane from the distillation bottom product.

7. A process according to claim 6 wherein the azeotrope mixture of hydrogen fluoride and 1,1-dichloro-1-fluoroethane distilled from the 1,1-dichloro-1-fluoroethane-enriched lower liquid phase is recycled to and combined with the initial distillation bottom product.

8. A process according to claim 2 wherein the first hydrogen fluoride-enriched upper liquid phase is recycled to and combined with the liquid mixture subject to initial distillation.

9. A process according to claim 2 wherein the second hydrogen fluoride-enriched upper liquid phase is recycled to and combined with the hydrofluorination reaction mixture.

10. A process according to claim 2 wherein the initial distillation bottom product is substantially free of 1-chloro-1,1-difluoroethane.

11. A process according to claim 10 wherein the initial distillation top product has a composition similar to the azeotropic composition of hydrogen fluoride and 1-chloro-1,1-difluoroethane, and the initial distillation bottom product has a composition similar to the azeotropic composition of hydrogen fluoride and 1,1-dichloro-1-fluoroethane.

12. A process according to claim 11 wherein the liquid mixture subject to separation contains, based upon the combined weight of 1,1-dichloro-1-fluoroethane and 1-chloro-1,1-difluoroethane in said mixture, from about 30 weight % to about 85 weight % of 1,1-dichloro-1-fluoroethane.

13. A process according to claim 12 wherein the liquid mixture subject to separation contains, based upon the combined weight of 1,1-dichloro-1-fluoroethane and 1-chloro-1,1-difluoroethane in said mixture, from about 50 weight % to about 85 weight % of 1,1-dichloro-1-fluoroethane.

14. A process for separating 1,1-dichloro-1-fluoroethane, 1-chloro-1,1-difluoroethane and hydrogen fluoride from a liquid mixture thereof, comprising:
   (a) from a reaction mixture for treating hydrogen fluoride with a co-reactant selected from the group consisting essentially of 1,1,1-trichloroethane, vinylidene chloride and combinations thereof, withdrawing as a reaction product stream a mixture comprising hydrogen fluoride, 1,1-dichloro-1-fluoroethane and 1-chloro-1,1-difluoroethane;
   (b) distilling the mixture to form a first overhead stream comprising 1-chloro-1,1-difluoroethane and hydrogen fluoride, and a first bottom stream comprising 1,1-dichloro-1-fluoroethane and hydrogen fluoride substantially free of 1-chloro-1,1-difluoroethane;

(c) cooling the first overhead stream to separate said overhead stream into a first hydrogen fluoride-enriched liquid phase and a 1-chloro-1,1-difluoroethane-enriched liquid phase, and separating the two phases to form a first hydrogen fluoride-enriched stream and a 1-chloro-1,1-difluoroethane-enriched stream;

(d) cooling the first bottom stream to separate said bottom stream into a second hydrogen fluoride-enriched liquid phase and a 1,1-dichloro-1-fluoroethane-enriched liquid phase, and separating the two phases to form a second hydrogen fluoride-enriched stream and a 1,1-dichloro-1-fluoroethane-enriched stream;

(e) distilling an azeotrope of hydrogen fluoride and 1-chloro-1,1-difluoroethane from the 1-chloro-1,1-difluoroethane-enriched stream, and recovering 1-chloro-1,1-difluoroethane from the azeotrope distillation bottom stream;

(f) recycling the azeotrope of hydrogen fluoride and 1-chloro-1,1-difluoroethane to the first overhead stream:

(g) distilling an azeotrope of hydrogen fluoride and 1,1-dichloro-1-fluoroethane from the 1,1-dichloro-1-fluoroethane-enriched stream, and recovering 1,1-dichloro-1-fluoroethane from the azeotrope distillation bottom stream;

(h) recycling the azeotrope of hydrogen fluoride and 1,1-dichloro-1-fluoroethane to the first bottom stream;

(i) recycling the first hydrogen fluoride-enriched stream to the reaction product stream; and (j) recycling the second hydrogen fluoride-enriched stream to the reaction mixture.

15. A process according to claim 14 wherein the first overhead stream has a composition similar to the azeotropic composition of the mixture of hydrogen fluoride and 1-chloro-1,1-difluoroethane, and the first bottom stream has a composition similar to the azeotropic composition of the mixture of hydrogen fluoride and 1,1-dichloro-1-fluoroethane.

16. A process according to claim 14 wherein the reaction product stream subject to separation contains, based upon the combined weight of 1,1-dichloro-1-fluoroethane and 1-chloro-1,1-difluoroethane contained therein, from about 30 weight % to about 85 weight % of 1,1-dichloro-1-fluoroethane.

17. A process according to claim 16 wherein the reaction product stream subject to separation contains, based upon the combined weight of 1,1-dichloro-1-fluoroethane and 1-chloro-1,1-difluoroethane contained therein, from about 50 weight % to about 85 weight % of 1,1-dichloro-1-fluoroethane.

* * * * *